United States Patent
Matsuo

(10) Patent No.: US 10,488,820 B2
(45) Date of Patent: Nov. 26, 2019

(54) DIGITAL HOLOGRAPHIC IMAGE-TAKING APPARATUS

(71) Applicant: OLYMPUS CORPORATION, Hachioji-shi, Tokyo (JP)

(72) Inventor: Keigo Matsuo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 3 days.

(21) Appl. No.: 15/844,009

(22) Filed: Dec. 15, 2017

(65) Prior Publication Data
US 2018/0107159 A1    Apr. 19, 2018

Related U.S. Application Data

(63) Continuation of application No. PCT/JP2015/003425, filed on Jul. 7, 2015.

(51) Int. Cl.
*G03H 1/04* (2006.01)
*G03H 1/00* (2006.01)
(Continued)

(52) U.S. Cl.
CPC ......... *G03H 1/0408* (2013.01); *G01N 21/453* (2013.01); *G02B 5/1809* (2013.01);
(Continued)

(58) Field of Classification Search
CPC .... G03H 1/0408; G03H 1/0443; G03H 1/041; G03H 1/0465; G03H 1/00;
(Continued)

(56) References Cited

U.S. PATENT DOCUMENTS 5,339,152 A * 8/1994 Horn ................ G01B 11/164
356/458
6,118,589 A * 9/2000 Angelo ................ G02B 5/045
359/621
(Continued)

FOREIGN PATENT DOCUMENTS

JP    2003240993 A    8/2003
JP    2011502256 A    1/2011
(Continued)

OTHER PUBLICATIONS

Peixeiro et al, Digital holography: benchmarking coding standards and representation formats (Year: 2016).*
(Continued)

*Primary Examiner* — Shan E Elahi
(74) *Attorney, Agent, or Firm* — Holtz, Holtz & Volek PC

(57) ABSTRACT

A digital holographic image-taking apparatus includes an illumination portion having a light emission surface for emitting illumination light toward an object, the illumination light having a specific wavelength in a coherent plane waveform; and an image sensor having an pixel array including two-dimensionally arranged pixels, the image sensor capturing an interference pattern generated based on the illumination light having acted on the object, in which the following conditional expression is satisfied: $0.0000001 < Z^2/S < 16$, where S represents the area of the light emission surface, and Z represents the distance from the light emission surface to the pixel array.

19 Claims, 18 Drawing Sheets

(51) Int. Cl.
  *G01N 21/45* (2006.01)
  *G02B 5/18* (2006.01)
  *G02B 5/20* (2006.01)
  *G02B 5/32* (2006.01)
  *F21V 8/00* (2006.01)

(52) U.S. Cl.
  CPC ............... *G02B 5/201* (2013.01); *G02B 5/32* (2013.01); *G03H 1/00* (2013.01); *G03H 1/041* (2013.01); *G03H 1/0443* (2013.01); *G03H 1/0465* (2013.01); *G02B 6/0035* (2013.01); *G03H 2001/0413* (2013.01); *G03H 2001/0436* (2013.01); *G03H 2001/0447* (2013.01); *G03H 2001/0452* (2013.01); *G03H 2001/0471* (2013.01); *G03H 2222/18* (2013.01); *G03H 2222/22* (2013.01); *G03H 2223/15* (2013.01); *G03H 2223/16* (2013.01); *G03H 2223/23* (2013.01)

(58) Field of Classification Search
  CPC ... G03H 2001/0452; G03H 2001/0447; G03H 2222/18; G03H 2001/0471; G03H 2001/0436; G03H 2223/23; G03H 2222/22; G03H 2223/15; G03H 2223/16; G03H 2001/0413; G01N 21/453; G02B 21/00
  USPC ......................................................... 348/41
  See application file for complete search history.

(56) References Cited

U.S. PATENT DOCUMENTS

| | | | | |
|---|---|---|---|---|
| 6,288,843 B1* | 9/2001 | Angelo | ................... | G02B 5/045 359/245 |
| 6,618,051 B1* | 9/2003 | Edwards | ................... | G03H 1/00 345/427 |
| 7,016,604 B2* | 3/2006 | Stavely | ................... | G03B 13/32 348/349 |
| 7,127,109 B1* | 10/2006 | Kim | ................... | G03H 1/0005 382/210 |
| 7,337,957 B2* | 3/2008 | Ashizaki | ................... | G03H 1/268 235/382 |
| 7,551,750 B2* | 6/2009 | D'Amato | ............ | G03H 1/0011 216/22 |
| 7,652,809 B2* | 1/2010 | Waldman | ................... | G03H 1/16 359/11 |
| 8,428,331 B2* | 4/2013 | DiMarzio | ............ | G02B 21/18 382/133 |
| 8,502,867 B2* | 8/2013 | Park | ................... | G01N 15/1434 348/135 |
| 8,542,421 B2* | 9/2013 | Rosen | ................... | G03B 35/02 359/9 |
| 9,465,228 B2* | 10/2016 | Lee | ................... | G02B 27/58 |
| 9,581,961 B2* | 2/2017 | Sato | ................... | G01B 9/02047 |
| 9,804,563 B2* | 10/2017 | Rosen | ................... | G03B 35/02 |
| 9,810,894 B2* | 11/2017 | Grier | ................... | G01N 15/0227 |
| 2003/0223616 A1* | 12/2003 | D'Amato | ............ | G03H 1/0011 382/100 |
| 2005/0129281 A1* | 6/2005 | Ashizaki | ................ | G03H 1/268 382/112 |
| 2005/0276592 A1* | 12/2005 | Stavely | ................... | G03B 13/32 396/111 |
| 2007/0187510 A1* | 8/2007 | Kotlarsky | .......... | G06K 7/10683 235/462.1 |
| 2008/0032325 A1* | 2/2008 | DiMarzio | .......... | G02B 21/0004 435/29 |
| 2010/0142014 A1* | 6/2010 | Rosen | ................... | G03B 35/02 359/1 |
| 2011/0043607 A1 | 2/2011 | Grier et al. | | |
| 2012/0194638 A1* | 8/2012 | Smalley | ................... | G03H 1/02 348/41 |
| 2012/0218379 A1 | 8/2012 | Ozcan et al. | | |
| 2013/0278981 A1 | 10/2013 | Huys et al. | | |
| 2013/0286678 A1 | 10/2013 | Sugiyama et al. | | |
| 2013/0293697 A1 | 11/2013 | Sun et al. | | |
| 2013/0335796 A1* | 12/2013 | Rosen | ................... | G03B 35/02 359/30 |
| 2014/0333935 A1* | 11/2014 | Grier | ................... | G01N 15/0227 356/457 |
| 2015/0293499 A1* | 10/2015 | Rosen | ................... | G03B 35/02 359/9 |
| 2015/0300803 A1 | 10/2015 | Horimai et al. | | |
| 2017/0155894 A1* | 6/2017 | Lee | ................... | G03H 1/268 |
| 2017/0329281 A1* | 11/2017 | Tagawa | ................... | G03H 1/0866 |
| 2018/0107158 A1* | 4/2018 | Watanabe | ................ | G03H 1/00 |
| 2019/0137932 A1* | 5/2019 | Ozcan | ................... | G03H 1/0005 |

FOREIGN PATENT DOCUMENTS

| | | |
|---|---|---|
| JP | 2013508775 A | 3/2013 |
| JP | 2013228735 A | 11/2013 |
| WO | 2011149405 A1 | 12/2011 |
| WO | 2013080488 A1 | 6/2013 |
| WO | 2014088089 A1 | 6/2014 |

OTHER PUBLICATIONS

International Search Report (ISR) and Written Opinion dated Oct. 13, 2015 issued in International Application No. PCT/JP2015/003425.

Japanese Office Action dated Jul. 23, 2019 (and English translation thereof) issued in counterpart Japanese Application No. 2017-526782.

* cited by examiner

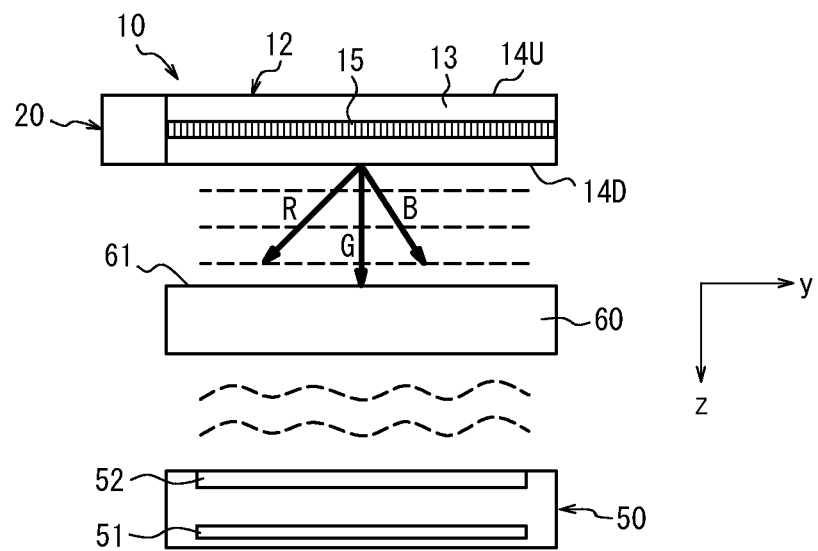
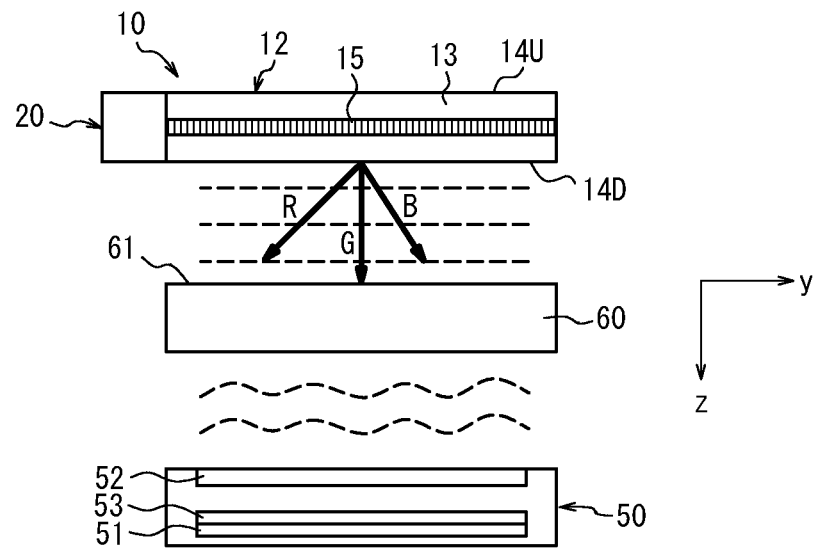

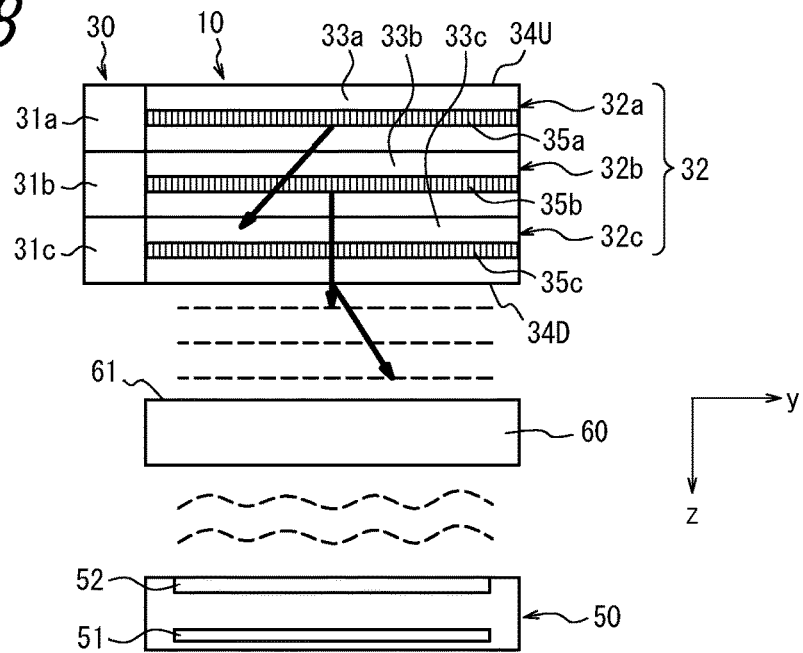
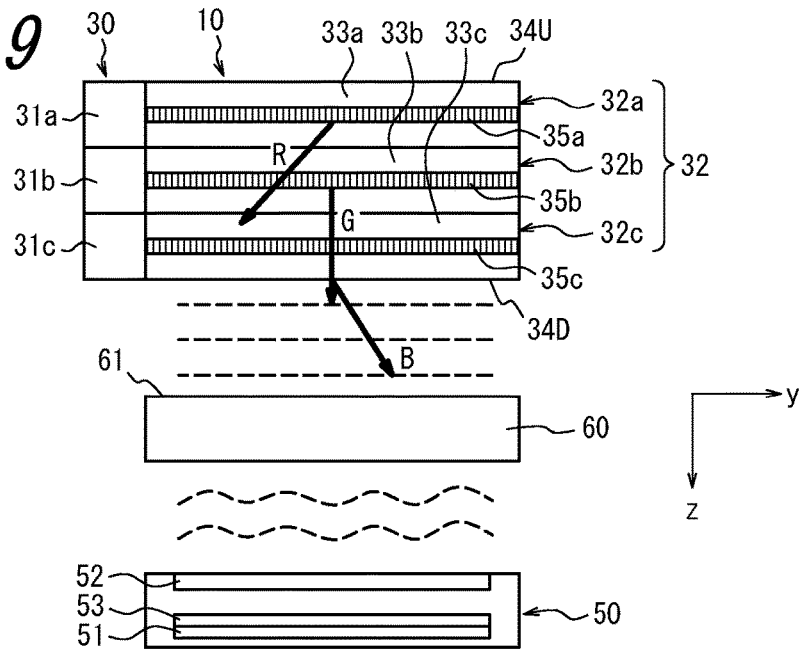

FIG. 11
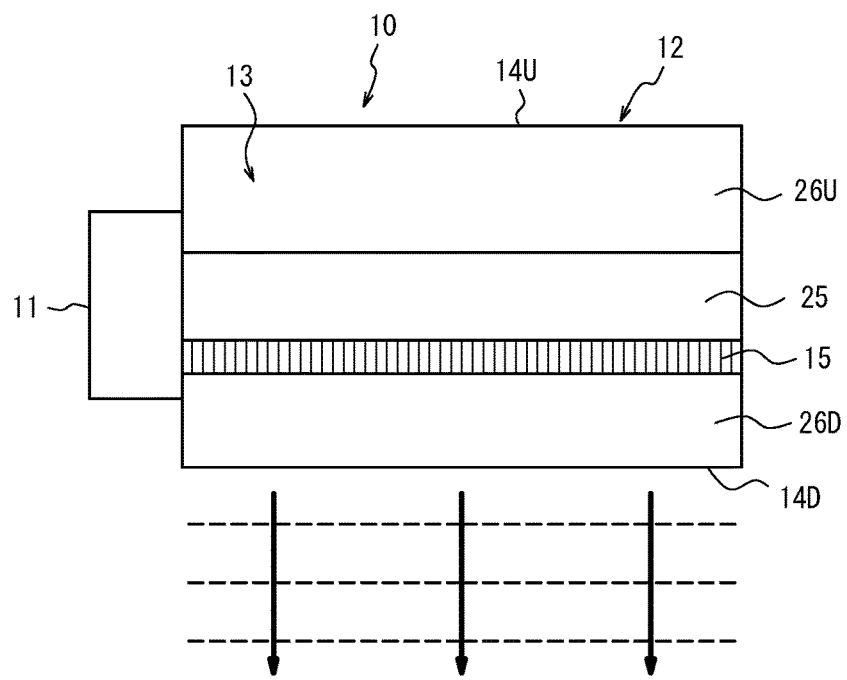
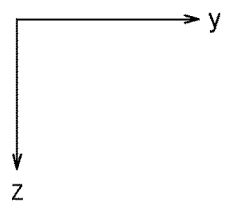

FIG. 13
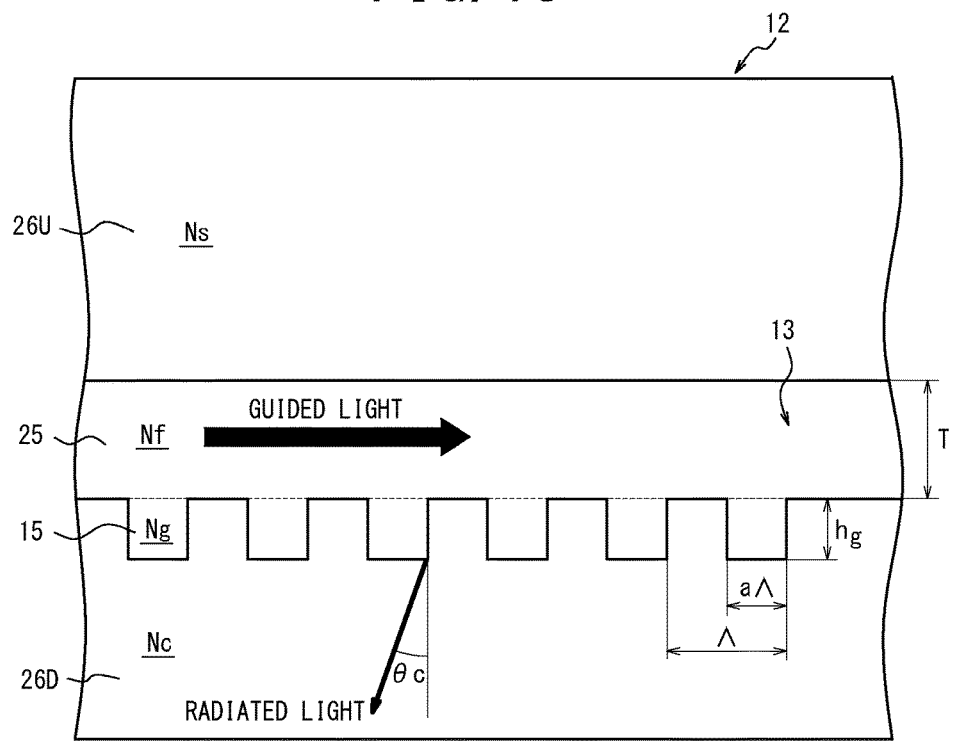
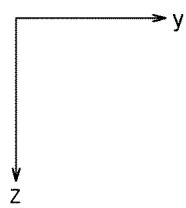

FIG. 15
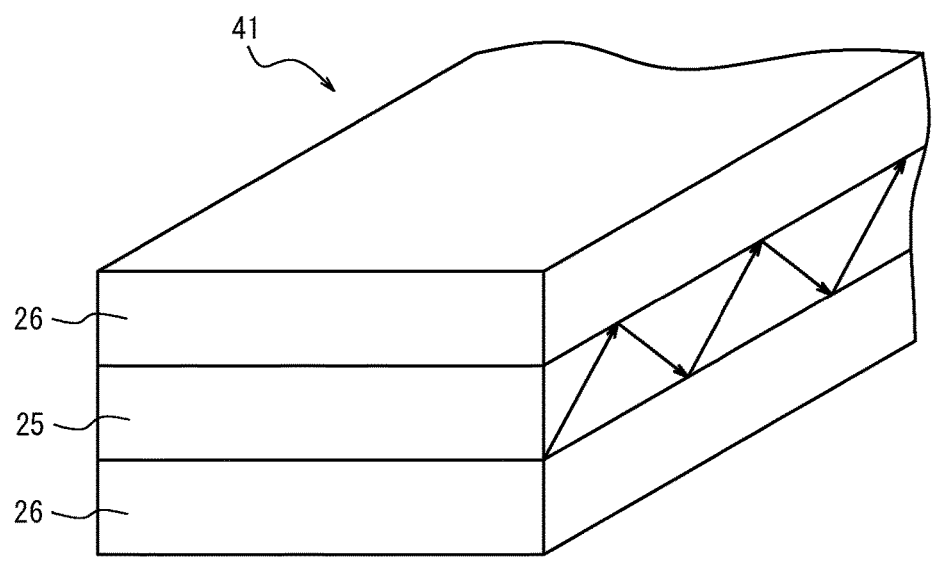
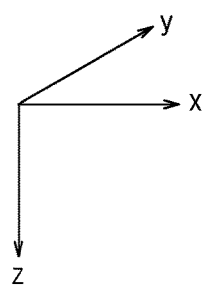

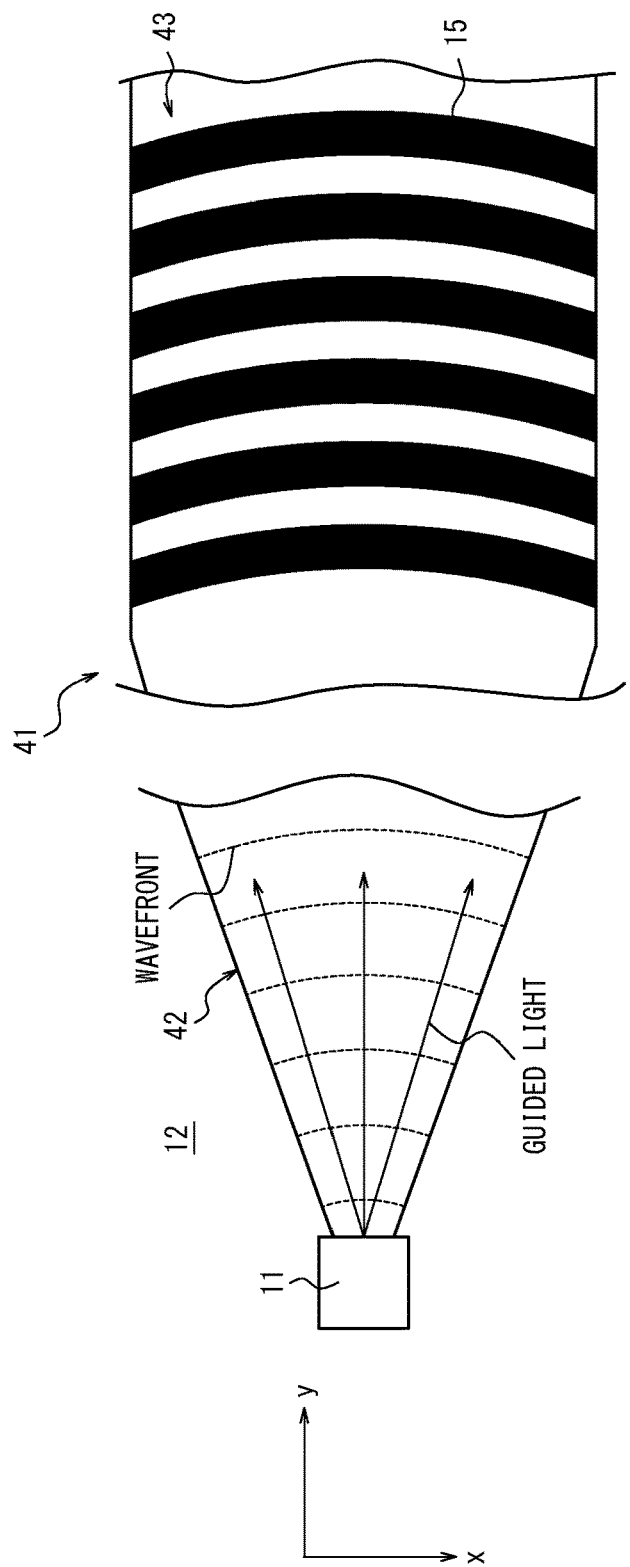

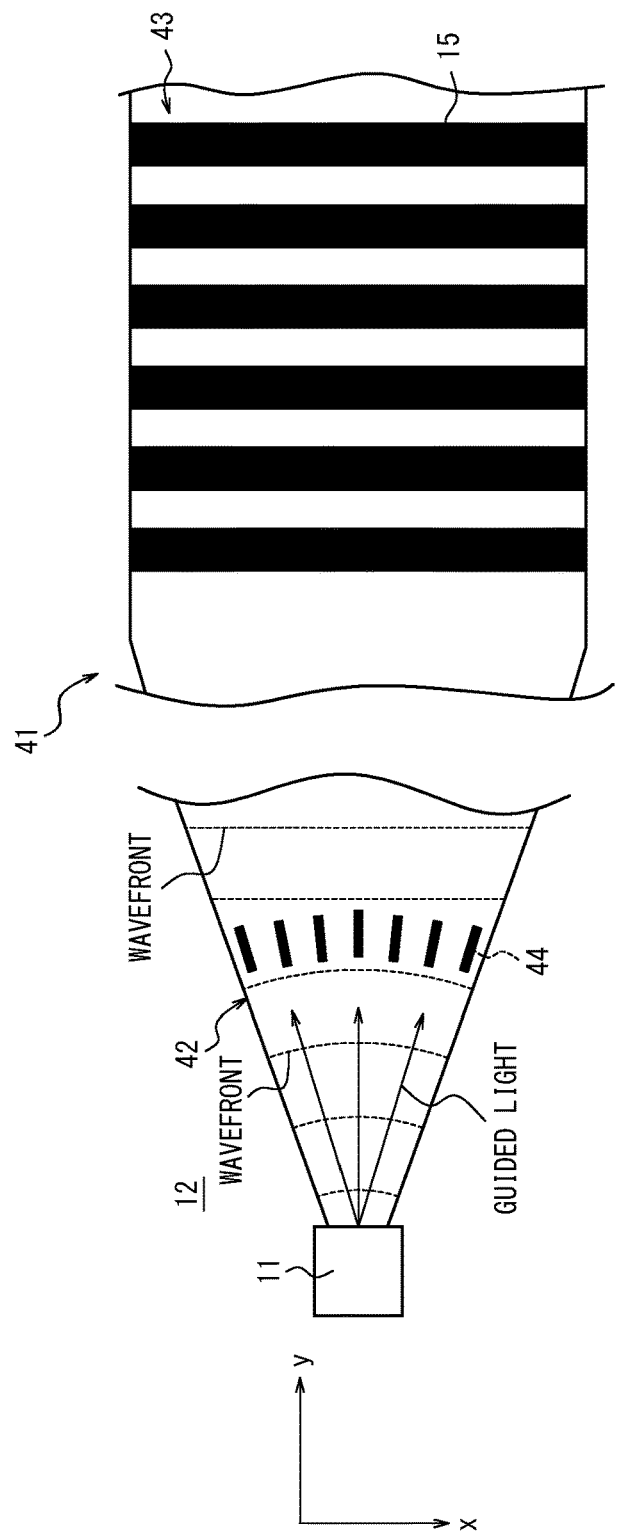

DIGITAL HOLOGRAPHIC IMAGE-TAKING APPARATUS

CROSS-REFERENCE TO RELATED APPLICATION

The present application is a Continuing Application based on International Application PCT/JP2015/003425 filed on Jul. 7, 2015, the content of which is incorporated herein by reference.

TECHNICAL FIELD

The disclosure relates to a digital holographic image-taking apparatus.

BACKGROUND

Digital holographic image-taking apparatuses are known as disclosed in, for example, in Patent Literature (PTL) 1 and PTL 2. PTL 1 discloses a digital holographic image-taking apparatus, which irradiates a sample with incoherent illumination light emitted from a light source formed of a light emitting diode, through a spatial filter having minute apertures, so as to capture, with the image sensor, an interference pattern formed between light passing through the sample and non-diffused light.

PTL 2 discloses a digital holographic image-taking apparatus, which irradiates a sample with coherent illumination light from a laser light source, and magnifies, via an object lens and an eyepiece lens, an interference pattern between light scattered by the sample and light not scattered by the sample, so as to capture an interference pattern by an image sensor.

CITATION LIST

Patent Literature

PTL 1: JP2013-508775A
PTL 2: JP2011-502256A

SUMMARY

Thus, the disclosed digital holographic image-taking apparatus includes:

an illumination portion having a light emission surface for emitting illumination light of a specific wavelength toward an object, the illumination light being in a coherent plane waveform; and an image sensor having an pixel array including two-dimensionally arranged pixels, the image sensor capturing an interference pattern generated based on the illumination light having acted on the object, in which the digital holographic image-taking apparatus satisfies the following conditional expression:

$0.0000001 < Z^2/S < 16$ where S represents the area of the light emission surface, and Z represents the distance from the light emission surface to the pixel array.

BRIEF DESCRIPTION OF THE DRAWINGS

In the accompanying drawings:

FIG. 6 is a schematic configuration diagram of an essential part of the digital holographic image-taking apparatus according to Embodiment 6;

FIG. 7 is a schematic configuration diagram of an essential part of the disclosed digital holographic image-taking apparatus according to Embodiment 7;

FIG. 8 is a schematic configuration diagram of an essential part of the disclosed digital holographic image-taking apparatus according to Embodiment 8;

FIG. 9 is a schematic configuration diagram of an essential part of the disclosed digital holographic image-taking apparatus according to Embodiment 9;

FIG. 11 is a schematic section of Configuration Example 1 of the disclosed illumination portion;

FIG. 13 explains the function of the illumination portion of FIG. 11;

FIG. 15 illustrates a basic structure of a slab optical waveguide in Configuration Example 3 of the disclosed illumination portion;

FIG. 16A is an enlarged schematic diagram of an optical waveguide optical system viewed from the z-direction, with the slab optical waveguide of FIG. 15;

FIG. 17A is an enlarged schematic diagram of an optical waveguide optical system viewed from the z-direction, the system having the slab optical waveguide in Configuration Example 4 of the illumination portion;

DETAILED DESCRIPTION

Hereinafter, Embodiments of the disclosed digital holographic image-taking apparatus are described, with reference to the drawings.

Embodiment 1

Figure 1:
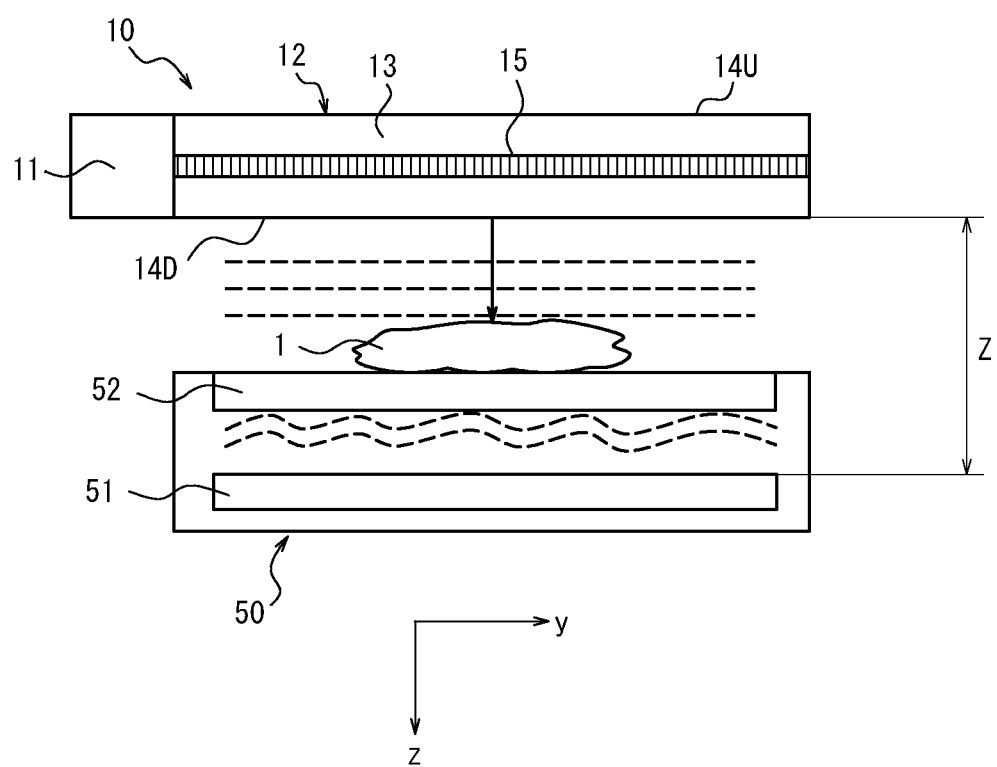
FIG. 1 is a schematic configuration diagram of an essential part of the disclosed digital holographic image-taking apparatus according to Embodiment 1.

FIG. 1 is a schematic configuration diagram of an essential part of the disclosed digital holographic image-taking apparatus according to Embodiment 1. The digital holographic image-taking apparatus according to Embodiment 1 includes an illumination portion 10 and an image sensor 50. The illumination portion 10 includes a light source 11 that emits illumination light having a coherent specific wavelength, and an optical waveguide optical system 12.

The light source 11 is configured by including a semiconductor laser. The optical waveguide optical system 12 includes: an optical waveguide 13 that propagates the illumination light from the light source 11 by causing the illumination light to be repeatedly reflected alternately between two planes vertically opposing in parallel to each other; and a grating part 15 that diffracts the illumination light propagating through the optical waveguide 13 so as to cause the illumination light to be emitted in a plane waveform in the same direction from a light emission surface 14D. The illumination light diffracted by the grating part 15 is also emitted in a plane waveform from a light emission surface 14U opposing to the light emission surface 14D. In FIG. 1, the optical waveguide optical system 12 is schematically illustrated in section in the y-z plane where the illumination light is propagated through the optical waveguide 13 in the y-direction and the light emission surface 14D has the normal direction thereof in the z-direction. The configuration of the illumination portion 10 is described later in detail.

The image sensor 50 is disposed as opposed to the light emission surface 14D as one of the light emission surfaces of the optical waveguide 13. The image sensor 50 includes a pixel array 51 of two-dimensionally arranged pixels along a plane substantially parallel to the light emission surface 14D and a cover glass 52 disposed on the incident surface side of the pixel array 51. The cover glass 52 is formed of a material transmissive to the illumination light emitted from the light emission surface 14D. In Embodiment 1, the cover glass 52 also serves as an object holder, which holds a transparent object 1, such as cells, having a refractive index directly placed on an upper surface of the cover glass 52 in a detachable manner.

In FIG. 1, illumination light in a plane waveform emitted from the light emission surface 14D passes through the object 1 placed on the cover glass 52 of the image sensor 50, during which a 0-order light not affected by the object 1 and diffracted light affected by the object 1 form an interference pattern on the pixel array 51 of the image sensor 50. Accordingly, the interference pattern may be captured by the image sensor 50 and subjected to arithmetic processing, to thereby analyze the object 1.

In FIG. 1, Embodiment 1 satisfies: $0.0000001 < Z^2/S < 16$, where S represents the area of the light emission surface 14D and Z represents the distance from the light emission surface 14D to the pixel array 51 of the image sensor 50. Here, $Z^2/S$ of 0.0000001 or below makes it difficult to ensure the space to place the object 1 onto the cover glass 52 of the image sensor 50. Thus, $Z^2/S$ may be set to a value larger than 0.0000001, preferably 0.001 or larger. However, $Z^2/S$ of 16 or above makes it difficult to attain size reduction, and thus, $Z^2/S$ may be less than 16, preferably 4 or less, and more preferably 1 or less. In Embodiment 1, the area S of the light emission surface 14D of the illumination portion 10 is larger than the square of the distance Z from the light emission surface 14D to the pixel array 51 of the image sensor 50, and thus, an interference pattern can be captured over a wide field of view. Further, the area of a region where the pixel array 51 of the image sensor 50 is disposed may preferably at least 0.8-fold of the area S of the light emission surface 14D in terms of attaining a wider field of view.

The aforementioned configuration according to Embodiment 1 is compact enough to allow the light emission surface 14D to be brought closer to the object 1 while ensuring the space to place the object 1 onto the cover glass 52 of the image sensor 50, to thereby capture an interference pattern over a wide field of view. In particular, Embodiment 1 is configured as a lens-less configuration with no lens disposed between the image sensor 50 and the object 1, which is advantageous in size reduction and cost reduction.

Embodiment 2

Figure 2:
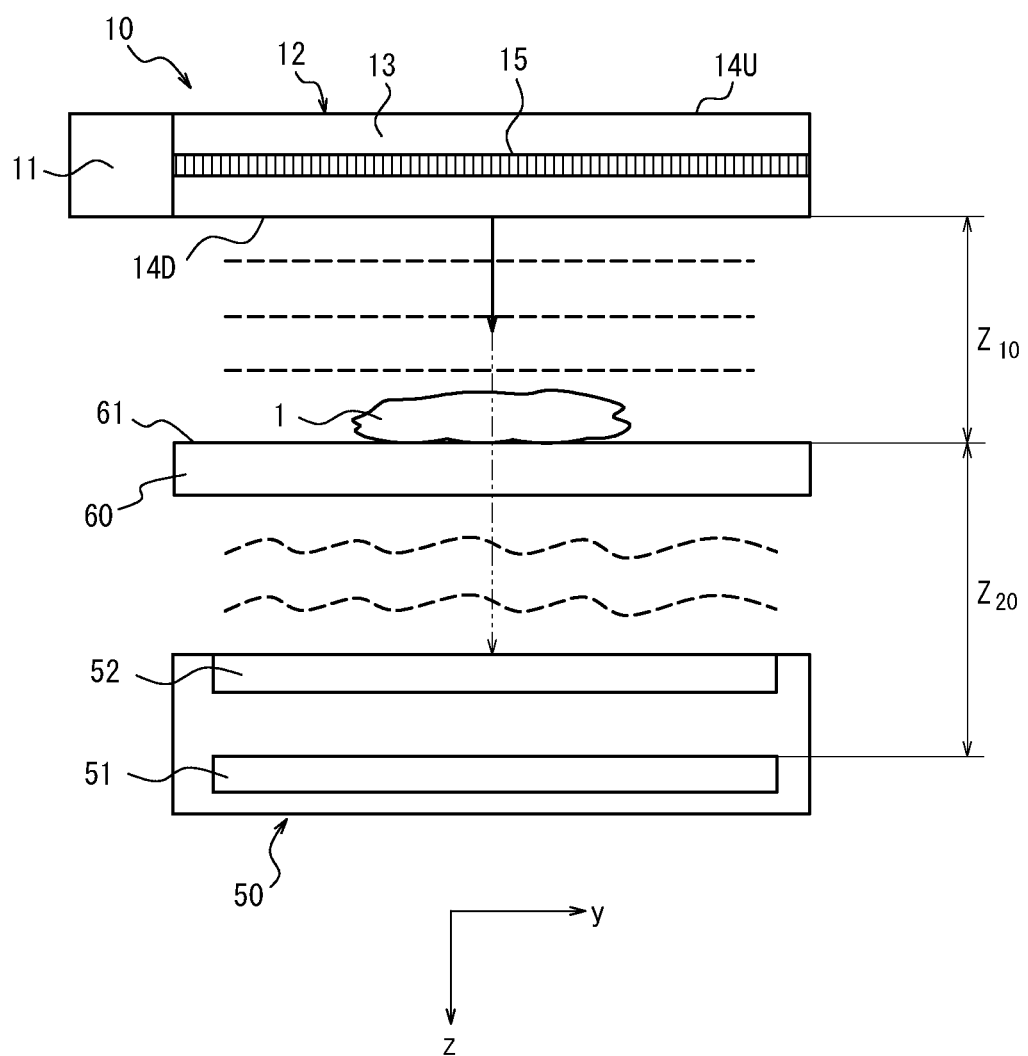
FIG. 2 is a schematic configuration diagram of an essential part of the disclosed digital holographic image-taking apparatus according to Embodiment 2.

FIG. 2 is a schematic configuration diagram of an essential part of the disclosed digital holographic image-taking apparatus according to Embodiment 2. The digital holographic image-taking apparatus according to Embodiment 2 further includes, in the configuration of FIG. 1, an object holder 60 disposed between the light emission surface 14D of the illumination portion 10 and the image sensor 50. The object holder 60 is formed of a material transmissive to the illumination light emitted from the illumination portion 10, and holds the object 1 detachably placed on a surface (object contact surface) 61 on the light emission surface 14D side.

In FIG. 2, Embodiment 2 satisfies: $0.0000001 < Z_{10}^2/S < 4$; and $0.0000001 < Z_{20}^2/S < 4$, where S represents the area of the light emission surface 14D of the illumination portion 10, $Z_{10}$ represents the distance from the light emission surface 14D to the object contact surface 61 of the object holder 60, and $Z_{20}$ represents the distance from the object contact surface 61 to the pixel array 51 of the image sensor 50. Therefore, Embodiment 2 also satisfies $0.0000001 < Z^2/S < 16$ of Embodiment 1. The rest of the configuration is similar to that of Embodiment 1, and thus the description thereof is omitted.

Here, $Z_{10}^2/S$ of 0.0000001 or below makes it difficult to ensure the space to place the object 1 onto the object holder 60. Thus, $Z_{10}^2/S$ may be set to a value larger than 0.0000001, preferably 0.001 or larger. However, $Z_{10}^2/S$ of 4 or above makes it difficult to attain size reduction, and thus, $Z_{10}^2/S$ may be less than 4, preferably 1 or less, and more preferably 0.5 or less. Similarly, $Z_{20}^2/S$ of 0.0000001 or below makes it difficult to ensure the space to dispose the object holder 60. Thus, $Z_{20}^2/S$ may be set to a value larger than 0.0000001, preferably 0.001 or larger. However, $Z_{20}^2/S$ of 4 or above makes it difficult to attain size reduction, and thus, $Z_{20}^2/S$ may be less than 4, preferably 1 or less, and more preferably 0.5 or less. Further, $Z_{10}$ and $Z_{20}$ may preferably satisfy $0.25 < Z_{10}/Z_{20} < 4$.

The aforementioned configuration according to Embodiment 2 is compact enough to allow the light emission surface 14D to be brought closer to the object 1 while ensuring the space to dispose the object 1 and the object holder 60, to thereby capture an interference pattern over a wide field of view.

Embodiment 3

Figure 3:
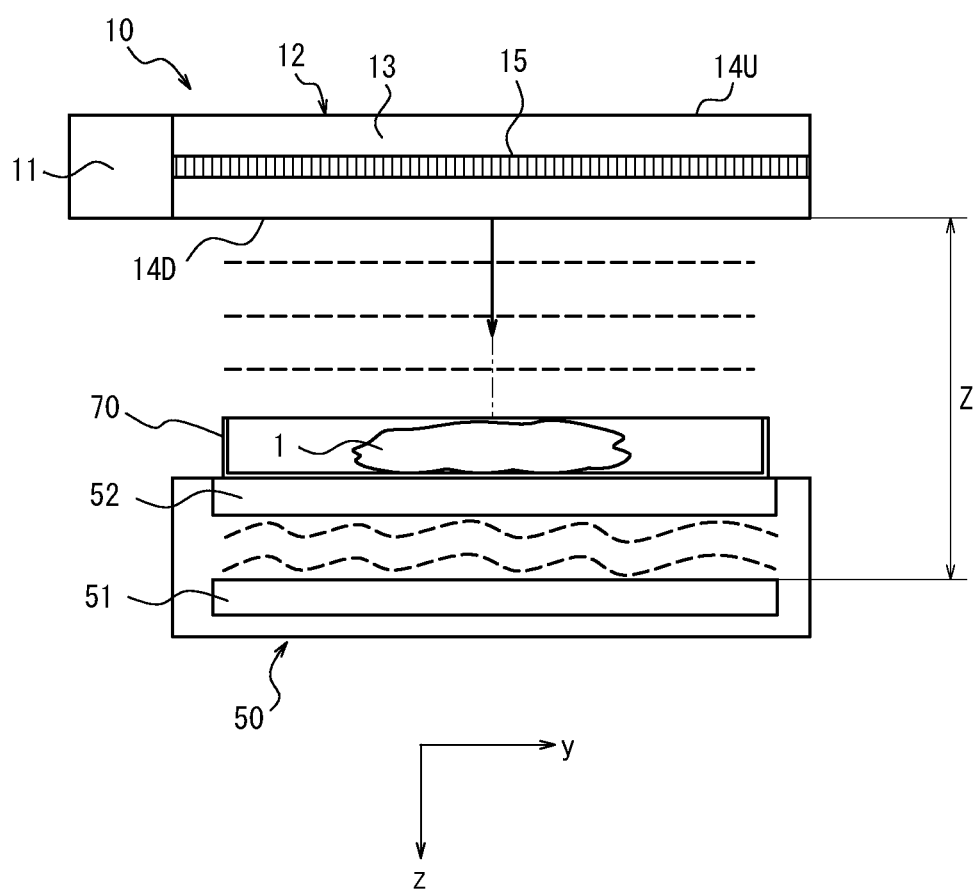
FIG. 3 is a schematic configuration diagram of an essential part of the disclosed digital holographic image-taking apparatus according to Embodiment 3.

FIG. 3 is a schematic configuration diagram of an essential part of the disclosed digital holographic image-taking apparatus according to Embodiment 3. The digital holographic image-taking apparatus according to Embodiment 3 is different from the configuration of FIG. 1 in that the object 1 is accommodated in a container 70 and placed on the cover glass 52 of the image sensor 50. The container 70 is formed of a material transmissive to the illumination light emitted from the light emission surface 14D. Examples available as the container 70 may include, for example, a vent cap flask, a well plate, or a dish, which are used in tissue culture or the like.

In FIG. 3, Embodiment 3 satisfies, as in Embodiment 1: $0.0000001 < Z^2/S < 16$, where S represents the area of the light emission surface 14D of the illumination portion 10, and Z represents the distance from the light emission surface 14D to the pixel array 51 of the image sensor 50. Here, $Z^2/S$ of 0.0000001 or below makes it difficult to ensure a space to place the container 70 accommodating the object 1, and thus, $Z^2/S$ may be set to a value larger than 0.0000001, preferably 0.001 or larger. However, $Z^2/S$ of 16 or above makes it difficult attain size reduction, and thus, $Z^2/S$ may be less than 16, preferably 4 or less, and more preferably 1 or less. The rest of the configuration is similar to that of Embodiment 1, and thus the description thereof is omitted.

The aforementioned configuration according to Embodiment 3 is compact enough to allow the light emission surface 14D to be brought closer to the object 1 while ensuring the space to place the container 70 accommodating the object 1, to thereby capture an interference pattern over a wide field of view.

Embodiment 4

Figure 4:
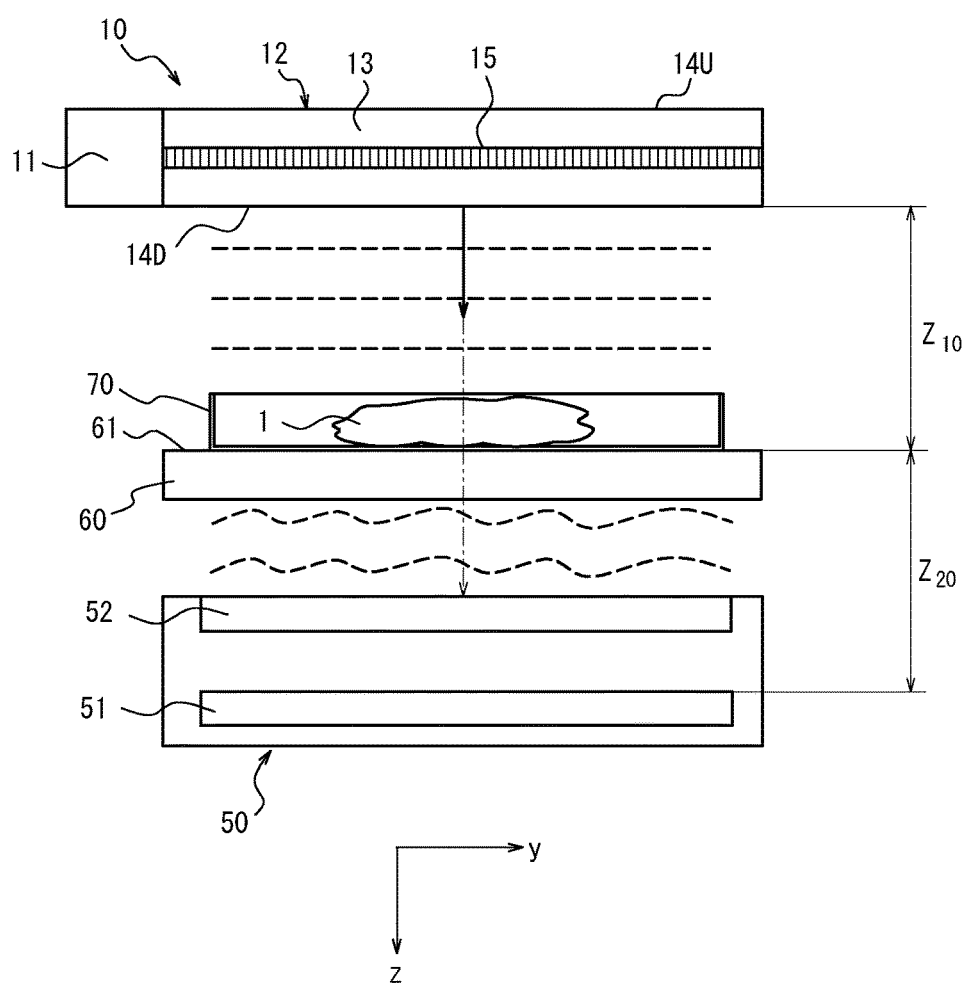
FIG. 4 is a schematic configuration diagram of an essential part of the disclosed digital holographic image-taking apparatus according to Embodiment 4.

FIG. 4 is a schematic configuration diagram of an essential part of the disclosed digital holographic image-taking apparatus according to Embodiment 4. The digital holographic image-taking apparatus of Embodiment 4 is different from the configuration of FIG. 2 in that the object 1 is accommodated in the container 70 and placed on the object contact surface 61 of the object holder 60. Accordingly, in Embodiment 4, the object 1 will be brought into contact with the object contact surface 61 through the bottom of the container 70. The container 70 is similarly configured as explained with reference to FIG. 3.

As in the case of Embodiment 2, Embodiment 3 satisfies: $0.0000001 < Z_{10}^2/S < 4$; and $0.0000001 < Z_{20}^2/S < 4$, where S represents the area of the light emission surface 14D of the illumination portion 10, $Z_{10}$ represents the distance from the light emission surface 14D to the object contact surface 61 of the object holder 60, and $Z_{20}$ represents the distance from the object contact surface 61 to the pixel array 51 of the image sensor 50. Therefore, Embodiment 4 also satisfies $0.0000001 < Z^2/S < 16$, which is explained with reference to Embodiment 1.

Here, $Z_{10}^2/S$ of 0.0000001 or below makes it difficult to ensure the space to place the container 70 accommodating the object 1 onto the object holder 60. Thus, $Z_{10}^2/S$ may be set to a value larger than 0.0000001, preferably 0.001 or larger. However, $Z_{10}^2/S$ of 4 or above makes it difficult to attain size reduction, and thus, $Z_{10}^2/S$ may be less than 4, preferably 1 or less, and more preferably 0.5 or less. Similarly, $Z_{20}^2/S$ of 0.0000001 or below makes it difficult to ensure the space to dispose the object holder 60. Thus, $Z_{20}^2/S$ may be set to a value larger than 0.0000001, preferably 0.001 or larger. However, $Z_{20}^2/S$ of 4 or above makes it difficult to attain size reduction, and thus, $Z_{20}^2/S$ may be less than 4, preferably 1 or less, and more preferably 0.5 or less. The rest of the configuration is similar to that of Embodiment 2, and thus the description thereof is omitted.

The aforementioned configuration according to Embodiment 4 is compact enough to allow the light emission surface 14D to be brought closer to the object 1 accommodated in the container 70 while ensuring the space to dispose the container 70 and the object holder 60, to thereby capture an interference pattern over a wide field of view.

Embodiment 5

Figure 5:
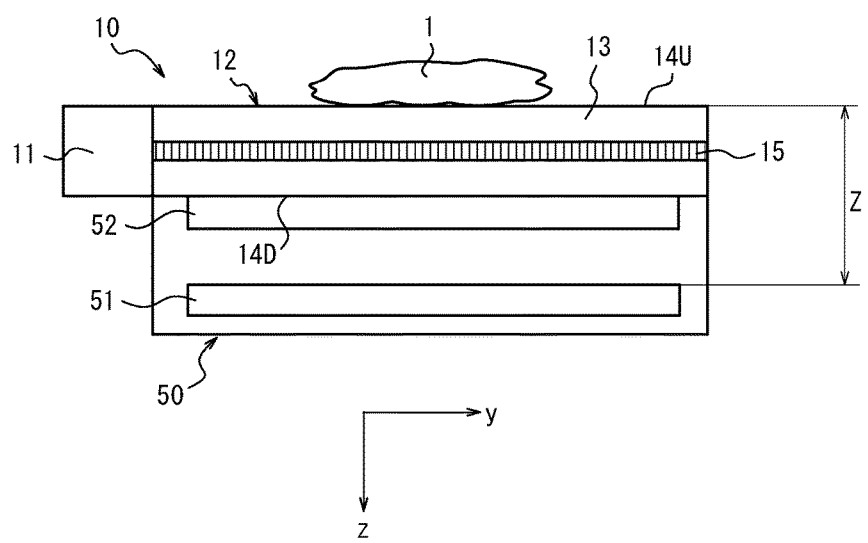
FIG. 5 is a schematic configuration diagram of an essential part of the disclosed digital holographic image-taking apparatus according to Embodiment 5.

FIG. 5 is a schematic configuration diagram of an essential part of the disclosed digital holographic image-taking apparatus according to Embodiment 5. The digital holographic image-taking apparatus according to Embodiment 5 is adapted to capture an interference pattern formed by the object 1 reflecting light, and includes, similarly to Embodiments above, the illumination portion 10 and the image sensor 50.

In Embodiment 5, the optical waveguide 13 of the illumination portion 10 is configured to serve as the object holder, to thereby detachably hold the object 1, directly or via the aforementioned container, on a light emission surface 14U, which is the other one of the light emission surfaces of the optical waveguide 13. FIG. 5 illustrates a case where the object 1 is directly held on the light emission surface 14U. The image sensor 50 is disposed as being joined to or spaced apart from but opposing to the light emission surface 14D of the optical waveguide 13. When the image sensor 50 is disposed as being joined to the light emission surface 14D, the cover glass 52 of the image sensor 50 may be omitted.

In FIG. 5, illumination light in a plane waveform emitted from the light emission surface 14U is reflected by the object 1 placed on the light emission surface 14U. The illumination light reflected by the object 1 passes through the optical waveguide 13 to be incident as object light onto the pixel array 51 of the image sensor 50. Meanwhile, illumination light in a plane waveform emitted from the light emission surface 14D is incident as reference light onto the pixel array 51. In this manner, an interference pattern between the object light and the reference light is formed on the pixel array 51, where the object light refers to light having acted on the object 1 or modulated by the object 1 and the reference light refers to light not having acted on the object 1 or not modulated by the object 1. Therefore, similarly to Embodiments above, the interference pattern may be captured by the image sensor 50 and subjected to arithmetic processing, to thereby analyze the object 1.

In FIG. 5, Embodiment 5 satisfies, similarly to Embodiments above, $0.0000001 < Z^2/S < 16$, where S represents the area of the light emission surfaces 14U and 14D and Z represents the distance from the light emission surface 14U, which emits illumination light to act on the object 1, to the pixel array 51 of the image sensor 50.

Embodiment 5 also satisfies $0 \le Z_{10}^2/S < 4$, and $0.0000001 < Z_{20}^2/S < 4$, where $Z_{10}$ represents the distance from the light emission surface 14U to the object contact surface and $Z_{20}$ represents the distance from the object contact surface 61 to the pixel array 51 of the image sensor 50. In Embodiment 5, the light emission surface 14U also serves as the object contact surface, and thus, $Z_{10}$ becomes 0, and accordingly $Z_{10}^2/S$ also becomes 0. On the other hand, when the object holder is separately disposed above the light emission surface 14U to hold the object, $Z_{10} > 0$ is established. Further, $Z_{20}$ becomes equal to Z.

Thus, as in Embodiment 5, when the object 1 is disposed on one of the light emission surfaces 14U and 14D of the optical waveguide 13 while the image sensor 50 is disposed on the other, there is no need to ensure the space to place the object 1 in particular. Therefore, in consideration of the structural dimensions of the optical waveguide 13 and the image sensor 50, proper values satisfying the aforementioned conditions may be selected, to thereby capture an interference pattern over a wide field of view with a compact configuration.

Here, specific numerical values for Z, $Z_{10}$, $Z_{20}$, and S in Embodiments 1 to 5 are exemplified in below. As one numeric example, the values may be given as: Z ($=Z_{10}+Z_{20}$)= 3 mm; $Z_{10}$=1 mm; $Z_{20}$=2 mm. S is defined as 1600 $mm^2$ (=40 mm×40 mm), on the premise that the image sensor 50 uses the light receiving area in full size of 40 mm×40 mm. In this case, $Z^2/S$=0.005625, $Z_{10}^2/S$=0.000625, $Z_{20}^2/S$=0.0025, $Z_{10}/Z_{20}$=0.5 are obtained.

As another numeric examples, Z=100 mm, $Z_{10}$=60 mm, $Z_{20}$=40 mm, S=1600 $mm^2$ may be established. In this case, $Z^2/S$=6.25, $Z_{10}^2/S$=2.25, $Z_{20}^2/S$=1, $Z_{10}/Z_{20}$=1.5 are obtained.

Embodiment 6

FIG. 6 is a schematic configuration diagram of an essential part of the digital holographic image-taking apparatus according to Embodiment 6. The digital holographic image-taking apparatus of Embodiment 6 is different from Embodiment 2 of FIG. 2 or Embodiment 4 of FIG. 4 in configuration of the illumination portion 10. The differences are described in below.

The illumination portion 10 includes: a light source portion 20 and the optical waveguide optical system 12. The light source portion 20 sequentially emits a plurality of coherent illumination lights of different peak wavelengths, and is configured to include a plurality of semiconductor lasers or a single wavelength tunable laser. For convenience of explanation, Embodiment 6 is described on the assumption that the light source portion 20 emits red (R) light, green (G) light, and blue (B) light.

The optical waveguide optical system 12 is used in common for R light, G light, and B light emitted from the light source portion 20. In the optical waveguide optical system 12, the grating part 15 is configured to emit, for example, G light substantially in the normal direction from the light emission surface 14D. Therefore, the grating part 15 diffracts R light and B light in a direction different from the direction of G light, and thus R light, G light, and B light will be emitted in different directions from the light emission surface 14D.

In Embodiment 6, R light, G light, and B light sequentially emitted from the illumination portion 10 respectively act on the object to form interference patterns, which are captured by the image sensor 50 through a frame sequential method.

According to Embodiment 6, interference patterns of the object are formed by lights of different wavelengths, which allows the object to be analyzed with high accuracy over a wide field of view, in addition to the effect of Embodiment 2 or Embodiment 4. Further, unlike the conventional cases, there is no need to mechanically shift the light source or the image sensor in order to vary the optical path length, which avoids complicating or enlarging the apparatus.

Embodiment 7

FIG. 7 is a schematic configuration diagram of an essential part of the disclosed digital holographic image-taking apparatus according to Embodiment 7. The digital holographic image-taking apparatus of Embodiment 7 simultaneously emits, in Embodiment 6, R light, G light, and B light from the light source portion 20 of the illumination portion 10, to thereby simultaneously irradiate the object with R light, G light, and B light. Therefore, in Embodiment 7, the light source portion 20 is configured by including three semiconductor lasers each emitting R light, G light, and B light, respectively.

Further, the image sensor 50 has, for example, a Bayer-arranged color filter 53 on the incident surface side of the pixel array 51, the color filter 53 having spectral sensitivity characteristics corresponding to R light, G light, and B light, and captures interference patterns of the object formed by R light, G light, and B light simultaneously emitted from the illumination portion 10. The rest of the configuration is similar to that of Embodiment 6, and thus the description thereof is omitted.

In Embodiment 7, the illumination portion 10 simultaneously emits R light, G light, and B light to irradiate the object, and the interference patterns of the object formed by the irradiation of lights are captured by the image sensor 50 via the color filter 53. Therefore, as compared with Embodiment 6 where the interference patterns are captured through a frame sequential method, the interference patterns of the object can be obtained as one frame, which allows for high-speed analysis.

Embodiment 8

FIG. 8 is a schematic configuration diagram of an essential part of the disclosed digital holographic image-taking apparatus according to Embodiment 8. The digital holographic image-taking apparatus of Embodiment 8 is different from Embodiment 2 of FIG. 2 or Embodiment 4 of FIG. 4 in configuration of the illumination portion 10. The differences are described in below.

The illumination portion 10 includes: a light source portion 30; and a plurality of layered optical waveguide optical systems 32. FIG. 8 illustrates, by way of example, three layered optical waveguide optical systems 32a, 32b, 32c. The light source portion 30 causes illumination lights of equal peak wavelength to be sequentially incident on the three optical waveguide optical systems 32a, 32b, and 32c.

The light source portion 30 is configured to have light sources each coupled to, for example, the three optical waveguide optical systems 32a, 32b, 32c, respectively, and to cause illumination lights of equal peak wavelength to be sequentially incident from the three light sources onto the corresponding one of the optical waveguide optical systems 32a, 32b, and 32c. Alternatively, the light source portion 30 is configured to have one light source, and to diverge the light emitted from the light source to cause the light thus diverged to be sequentially incident onto the three optical waveguide optical systems 32a, 32b, and 32c through a publicly-known optical shutter such as a liquid crystal shutter. FIG. 8 illustrates, by way of example, light sources 31a, 31b, 31c each coupled to the three optical waveguide optical systems 32a, 32b, 32c, respectively, so as to emit illumination lights of the same wavelength.

The optical waveguide optical systems 32a, 32b, 32c are configured similarly to the optical waveguide optical system 12 described above. In other words, the optical waveguide optical systems 32a, 32b, 32c include: optical waveguides 33a, 33b, 33c each propagating the illumination light from the corresponding one of the light sources 31a, 31b, 31c by causing the illumination light to be repeatedly reflected alternately between two planes vertically opposing in parallel to each other; and grating parts 35*a*, 35*b*, 35*c* each diffracting the illumination light propagating through the respective one of the optical waveguides 33*a*, 33*b*, 33*c* so as to cause the illumination light to be emitted in a plane waveform from the light emission surface 34D on the underside of the optical waveguide 33*c* in the lowermost layer. The grating parts 35*a*, 35*b*, 35*c* are configured to diffract and emit the illumination lights in different directions. Even in this case, illumination lights each diffracted by the grating parts 35*a*, 35*b*, 35*c* are also emitted in a plane waveform from the light emission surface 34U as the upper surface of the optical waveguide 33*a* opposing to the optical emission surface 34D.

According to Embodiment 8, the image sensor 50 captures, through a frame sequential method, images of interference patterns of the object each formed by the illumination lights of the same wavelength sequentially emitted in a plane waveform from the illumination light 10 in different directions. Therefore, the object can be analyzed with high precision over a wide field of view with single-colored illumination light, which avoids complicating or enlarging the apparatus. Further, the irradiation direction of the illumination light can be defined as appropriate depending on the configurations of the grating parts 35*a*, 35*b*, 35*c*, which can improve the freedom of design, to thereby adopt a configuration suited for the object.

Embodiment 9

FIG. 9 is a schematic configuration diagram of an essential part of the disclosed digital holographic image-taking apparatus according to Embodiment 9. The digital holographic image-taking apparatus according to Embodiment 9 simultaneously emits, in Embodiment 8, R light, G light, and B light in a coherent plane waveform from the illumination portion 10 toward the object. Accordingly, light sources 31*a*, 31*b*, 31*c* of the light source portion 30 are configured to emit R light, G light, and B light as illumination lights of different wavelengths.

The optical waveguide optical systems 32*a*, 32*b*, 32*c* are layered from the light emission surface 34D side opposing to the object holder 60, in the ascending order of the wavelength to be emitted. Therefore, the light source 31*a* coupled to the optical waveguide optical system 32*a*, the light source 31*b* coupled to the optical waveguide optical system 32*b*, and the light source 31*c* coupled to the optical waveguide optical system 32*c* each emit R light, G light, and B light, respectively. The grating parts 35*a*, 35*b*, 35*c* of the optical waveguide optical systems 32*a*, 32*b*, 32*c* are configured to diffract and emit R light, G light, and B light in different directions.

Further, as in Embodiment 7, the image sensor 50 has a color filter 53 on the incident surface side of the pixel array 51, the color filter 53 having spectral sensitivity characteristics corresponding to R light, G light, and B light, and captures interference patterns of the object formed by R light, G light, and B light simultaneously emitted from the illumination portion 10. The rest of the configuration is similar to that of Embodiment 8, and thus the description thereof is omitted.

According to Embodiment 8, the illumination portion 10 simultaneously emits R light, G light, and B light to irradiate the object, and the interference patterns of the object formed by the irradiation of lights are captured by the image sensor 50 via the color filter 53. Therefore, as in the case of Embodiment 7, the object can be advantageously analyzed over a wide field of view at high speed and with high precision. Further, the irradiation directions of R light, G light, and B light can be defined as appropriate depending on the configurations of the grating parts 35*a*, 35*b*, 35*c*, which can improve the freedom of design as in the case of Embodiment 8, to thereby adopt a configuration suited for the object.

Embodiment 10

Figure 10:
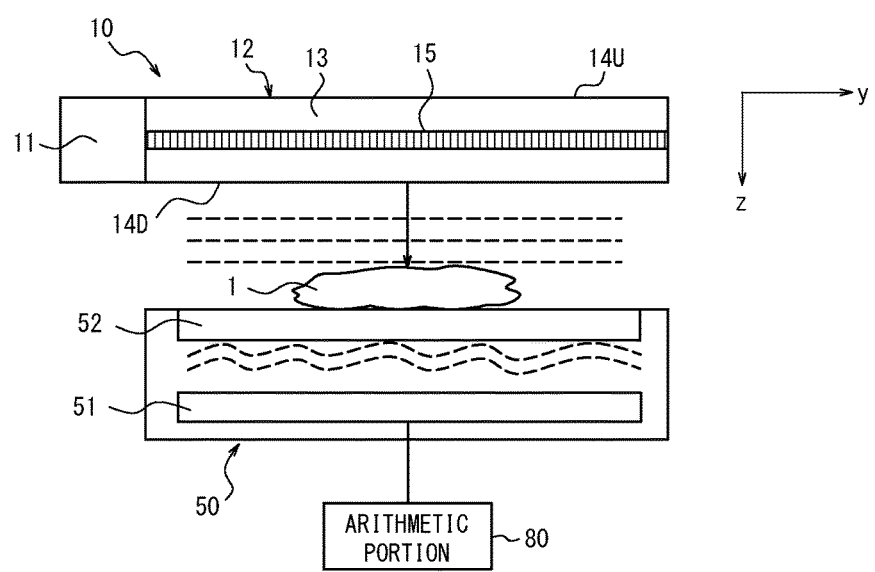
FIG. 10 is a schematic configuration diagram of an essential part of disclosed the digital holographic image-taking apparatus according to Embodiment 10.

FIG. 10 is a schematic configuration diagram of an essential part of disclosed the digital holographic image-taking apparatus according to Embodiment 10. The digital holographic image-taking apparatus according to Embodiment 10 includes, in Embodiment 1, an arithmetic portion 80 for analyzing the object 1 based on an output of the image sensor 50. The arithmetic portion 80 is configured as software to be executed on any suitable processor such CPU (central processing portion). The arithmetic portion 80 may be configured by a dedicated processor specialized in processing, such as DSP (digital signal processor).

As described above, the arithmetic portion 80 may be incorporated in the digital holographic image-taking apparatus, so as to analyze the object 1 with simple operation, as compared with the case where the arithmetic portion is externally attached.

Of Embodiments 1 to 10 described above, the illumination portion 10 of Embodiments 6 to 9 may be applied to Embodiment 1, Embodiment 3, or Embodiment 5 to form the digital holographic image-taking apparatus. Further, the arithmetic portion 80 of Embodiment 10 may similarly be provided to the digital holographic image-taking apparatus of Embodiments 2 to 9.

Next, Configuration Examples of the illumination portion 10 of Embodiments above are described in detail.

Configuration Example 1 of Illumination Portion

FIG. 11 is a schematic section of Configuration Example 1 of the disclosed illumination portion 10. The illumination portion 10 of FIG. 11 is used in, for example, Embodiments 1 to 7 and Embodiment 10, and has a single-layered optical waveguide optical system 12. As described above, the illumination portion 10 includes: the light source 11 or the light source portion 20; and the optical waveguide optical system 12. The optical waveguide optical system 12 includes: the optical waveguide 13 for propagating illumination light; and the grating part 15 for diffracting the illumination light propagating through the optical waveguide 13 to emit the illumination light in a plane waveform from the light emission surface 14D. FIG. 11 illustrates, by way of example, the light source 11 disposed as being coupled to the incident end of the optical waveguide 13. Further, the optical waveguide optical system 12 is illustrated in section in the y-z plane where illumination light is propagated through the optical waveguide 13 in the y-direction and the light emission surface 14D has the normal direction thereof in the z-direction.

The optical waveguide 13 is configured by including: a core 25; a clad 26U on the upper side of the core 25; and a clad 26D on the lower side of the core 25. The core 25 is formed to have an arbitrary shape in section in a direction orthogonal to the y-z plane, such as, for example, a circular section, an oval section, or a rectangular section. The clads 26U and 26D are formed at least above and below of the emission region of illumination light, around the core 25 except for the both ends thereof in the y-direction.

Figure 12A:
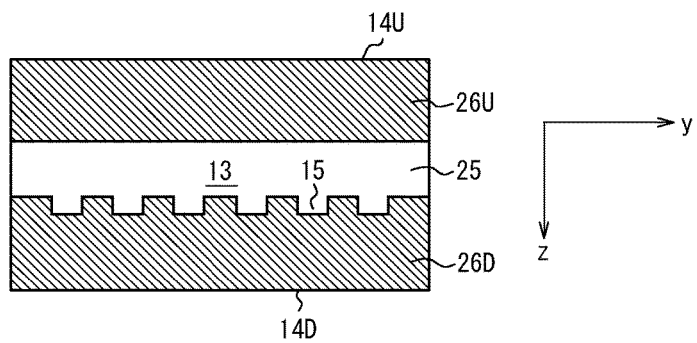
FIG. 12A is a diagram explaining a formation example of the grating of FIG. 11.
Figure 12B:
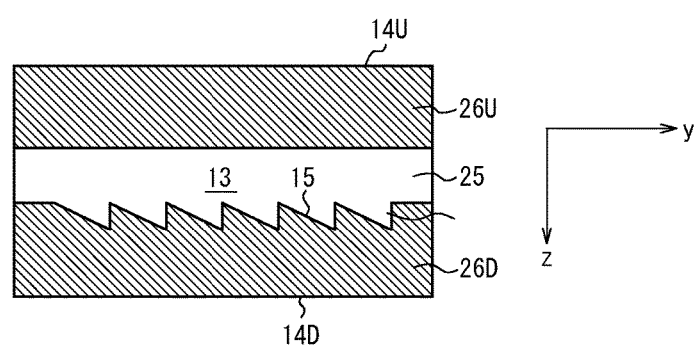
FIG. 12B is a diagram explaining a formation example of the grating of FIG. 11.
Figure 12C:
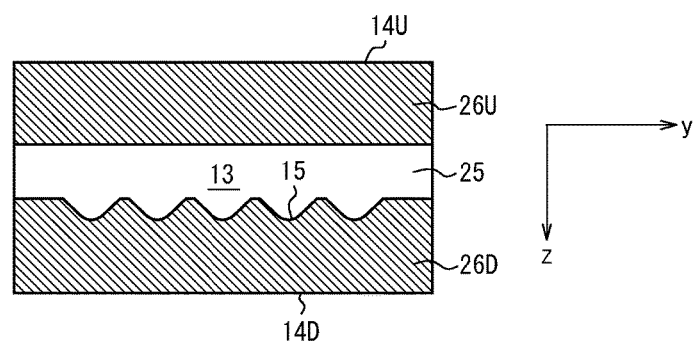
FIG. 12C is a diagram explaining a formation example of the grating of FIG. 11.
Figure 12D:
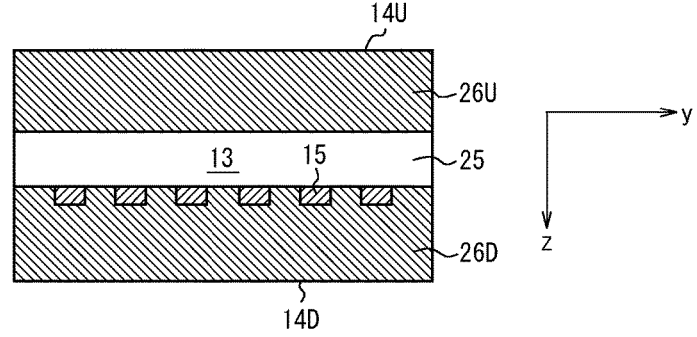
FIG. 12D is a diagram explaining a formation example of the grating of FIG. 11.

The grating part 15 is formed along the y-direction at an interface between the core 25 and the clad 26D or inside the core 25, in a propagation path of illumination light of the optical waveguide 13, so as to emit illumination light in a plane waveform in the z-direction. The grating part 15 may be formed at an interface between the core 25 and the clad 26U. The grating part 15 may be formed of, for example, rectangular grooves illustrated in FIG. 12A, sawtooth grooves as illustrated in FIG. 12B, waveform grooves as illustrated in FIG. 12C, or rectangular grooves with different refractive indices as illustrated in FIG. 12D.

Next, the function of the optical waveguide optical system 12 is described with reference to FIG. 13. The optical waveguide optical system 12 of FIG. 13 is configured by including: the core 25 formed with a thickness T and a refractive index Nf on the clad 26D on the lower side with a refractive index Ns; the grating part 15 with a refractive index Ng, a period Λ, a grating factor a, and a height hg, which is formed at the boundary with respect to the core 25; and further the clad 26U on the upper side with a refractive index Nc, which is layered on the core 25. The clad 26D, the core 25, and the clad 26U form the optical waveguide 13.

In FIG. 13, illumination light (wavelength λ) caused to incident into the optical waveguide 13 repeats total reflection at the interface between the core 25 and the clads 26D and 26U that are different in refractive index, so as to be confined therewithin to propagate through inside the optical waveguide 13 in a certain propagation mode. In the illumination light propagating inside the optical waveguide 13, when the conditional expression (1) below is satisfied in a portion where the grating part 15 with a period Λ is disposed, the propagation mode and the radiation mode are coupled to each other. As a result, when illumination light having a propagation constant $\beta_0$ propagates inside the optical waveguide 13 in the y-direction, a spatial harmonic wave with a propagation constant $\beta_q$ in the y-direction is generated along with the illumination light. At this time, illumination light propagating inside the optical waveguide 13 is radiated outside the illumination portion 10 in the radiation mode at a radiation angle (θc), as a plane wave in a band shape (one-dimensional form) having an area.

$$Nc \cdot k_0 \cdot \sin\theta_c = \beta_0 + qK \ (q = 0, \pm 1, \pm 2, \ldots) \quad (1)$$

$$\beta_0 = N_{\text{eff}} \cdot k_0$$

$$K = \frac{2\pi}{\Lambda}$$

where $k_0$ represents vacuum wave number, and $N_{\text{eff}}$ represents effective index of the illumination light.

The propagation mode of illumination light propagating through inside the optical waveguide 13 in the y-direction may be categorized into multimode propagation with a plurality of propagation constants and single mode propagation with only one propagation constant for the basic mode, depending on the parameter conditions (refractive index, thickness, wavelength) constituting the optical waveguide 13.

In Embodiments 1 to 5 and Embodiment 10, the illumination portion 10 only outputs a plane wave with a specific radiation angle (θc). In this case, the grating part 15 is formed with a period Λ which uniquely determines q in the expression (1) with respect to a specific propagation mode, to thereby propagate single mode light. With this configuration, light is emitted outside the optical waveguide 13 in a specific radiation mode along with the propagated light, which eventually allows the illumination portion 10 to exclusively emit a plane wave with a specific radiation angle.

For example, when the illumination light emitted from the light source 11 has a wavelength (λ) of λ=546.074 nm (G light), the core 25 and the grating part 15 are each defined to have a refractive index (Nf) and a refractive index (Ng), respectively, which satisfy Nf=Ng=1.5354, the clads 26D and 26U are defined to have refractive indices (Ns, Nc) satisfying Ns=Nc=1.46008, the core 25 is defined to have a thickness (T) of T=550 nm, and the grating part 15 is defined to have a period (Λ) of Λ=339 nm, to thereby form the optical waveguide 13. In this case, the optical waveguide 13 will have an effective refractive index $N_{\text{eff}}$ of $N_{\text{eff}}$=1.50788, and the illumination light will have a radiation angle (θc) of θc=−4.0°. The grating factor a and height hg are defined as a=0.5, hg=50 nm. The radiation angle θc of the illumination light may be 0° as well.

In Embodiment 6 and Embodiment 7, the optical waveguide 13 may similarly be configured. In this case, R light and B light are different in wavelength from G light, with the result that R light, G light, and B light are respectively emitted in different directions from the light emission surface 14D. Needless to say, the grating part 15 may include a grating configured to diffract R light, G light, and B light each in different directions.

The illumination portion 10 according to Configuration Example 1 is capable of emitting a band-shaped illumination light in a desired direction over a wide field of view, with a thin and compact configuration.

Configuration Example 2 of Illumination Portion

Figure 14:
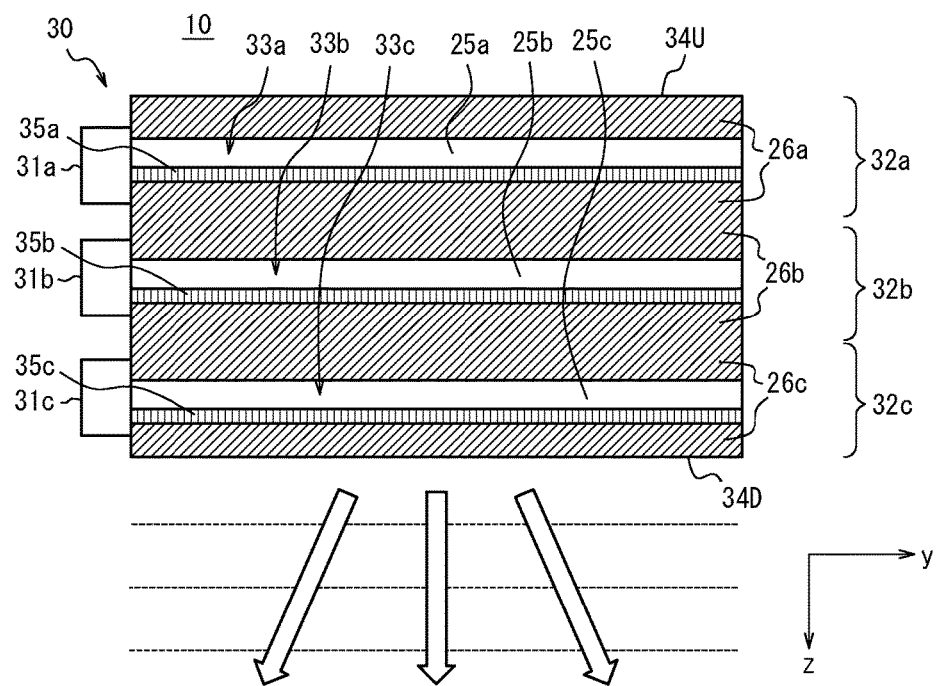
FIG. 14 is an explanatory diagram of Configuration Example 2 of the disclosed illumination portion.

FIG. 14 is a schematic section illustrating Configuration Example 2 of the illumination portion 10. The illumination portion 10 of FIG. 14 is used in, for example, Embodiment 8 and Embodiment 9, in which three optical waveguide optical systems 32a, 32b, 32c similarly configured as the optical waveguide optical system 12 of FIG. 11 are layered. The optical waveguide 33a includes the core 25a; the upper and lower clads 26a; and the grating part 35a. The optical waveguide 33b has the core 25b, the upper and lower clads 26b, and the grating part 35b. The optical waveguide 33c has the core 25c, the upper and lower clads 26c, and the grating part 35c. The lower clad 26a forming the optical waveguide 33a and the upper clad 26b forming the optical waveguide 33b are coupled to each other, and the lower clad 26b of the optical waveguide 33b and the upper clad 26c forming the optical waveguide 33c are coupled to each other.

When applied to the illumination portion 10 of Embodiment 8, the grating parts 35a, 35b, 35c are configured to have the period (Λ) so as to diffract and emit illumination lights of the same wavelength in desired directions different from one another.

When applied to the illumination portion 10 of Embodiment 9, the grating parts 35a, 35b, 35c are configured to have the period (Λ) so as to diffract and emit R light, G light, and B light in desired directions different from one another. In this case, as described above, the optical waveguide optical systems 32a, 32b, 32c are layered from the light emission surface 34D side opposing to the object holder 60, in the ascending order of the wavelength to be emitted. This configuration can prevent the generation of diffracted light in unnecessary orders, which may otherwise be generated when illumination light emitted from an optical waveguide optical system in the upper layer passes through an optical waveguide optical system in the lower layer.

The illumination portion 10 of Configuration Example 2 is also capable of emitting a band-shaped illumination light in desired different directions over a wide field of view, with a thin and compact configuration, similarly to the illumination portion 10 of Configuration Example 1.

Configuration Example 3 of Illumination Portion

The illumination portion 10 of Configuration Example 3 is different from Configuration Examples 1 and 2 in that the optical waveguide of the optical waveguide optical system is configured as a slab optical waveguide so as to emit illumination light of a plane wave in a sheet form (two-dimensional form) in a desired direction.

FIG. 15 illustrates a basic structure of a slab optical waveguide. The slab optical waveguide 41 has the core 25 in a plate shape, and the clad 26 layered on both sides of the core 25. In FIG. 15, when the propagation direction of illumination light is defined as y-direction, the thickness direction of the core is defined as z-direction, and a direction orthogonal to the y-direction and the z-direction is defined as x-direction, no clad is formed on both ends in the x-direction of the core 25 while the core 25 and the clad 26 bear refractive index difference in the z-direction. Illumination light introduced into the core 25 from the y-direction is confined within the core 25 due to the refractive index difference between the core 25 and the clad 26 and propagated in the y-direction.

Figure 16B:
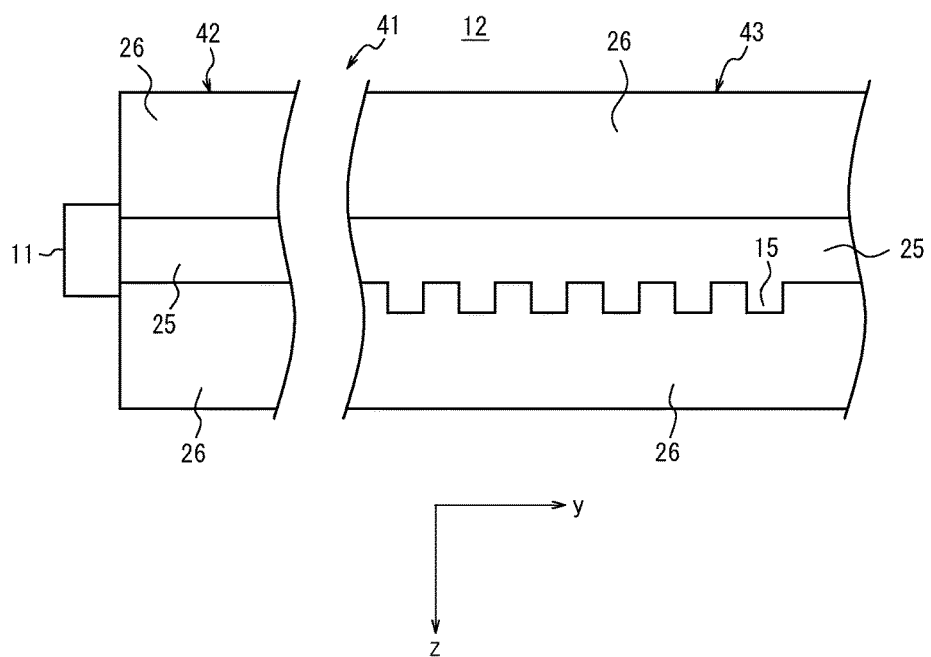
FIG. 16B is an enlarged schematic diagram of an optical waveguide optical system viewed from the x-direction, with the slab optical waveguide of FIG. 15.

FIGS. 16A and 16B illustrate the optical waveguide optical system 12 having the slab optical waveguide 41, where: FIG. 16A is an enlarged schematic diagram of the optical waveguide optical system 12 viewed from the z-direction; and FIG. 16B is an enlarged schematic diagram viewed from the x-direction. The slab optical waveguide 41 includes: a tapered optical waveguide 42 that expands in one end to the other end; and a rectangular optical waveguide 43 coupled to the expanded other end of the tapered optical waveguide 42. The tapered optical waveguide 42 and the rectangular optical waveguide 43 both have the core 25 extending along the x-y plane and the clad 26 formed on both sides opposing to each other in the z-direction of the core 25, with the grating part 15 formed on the rectangular optical waveguide 43. The tapered optical waveguide 42 and the rectangular optical waveguide 43 are, for example, integrally formed, and receive illumination light incident from an end face of the tapered optical waveguide 42, the end face being opposite to the rectangular optical waveguide 43. The tapered optical waveguide 42 of FIGS. 16A and 16B is illustrated, by way of example, as having the light source 11 coupled thereto, In FIGS. 16A and 16B, illumination light emitted from the light source 11 is confined in the z-direction in the tapered optical waveguide 42 and propagated in the y-direction. Further, illumination light incident on the tapered optical waveguide 42 is propagated as spreading in the x-direction as a spherical wave, so as to be enlarged in area. The grating part 15 is formed in a predetermined shape (rectangular in FIG. 16B) and with a predetermined period in the y-z plane, while being formed in a spherical shape in the x-y plane in line with the spherical wave of the illumination light.

When applied to the illumination portion 10 of Embodiment 8 and Embodiment 9 above, the optical waveguides 33a, 33b, 33c are each formed as a slab optical waveguide similar to those of FIG. 16A and FIG. 16B.

The illumination portion 10 according to Configuration Example 3 is capable of emitting illumination light in a sheet shape with a large area in a desired direction over a wide field of view, with a thin and compact configuration.

Configuration Example 4 of Illumination Portion

Figure 17B:
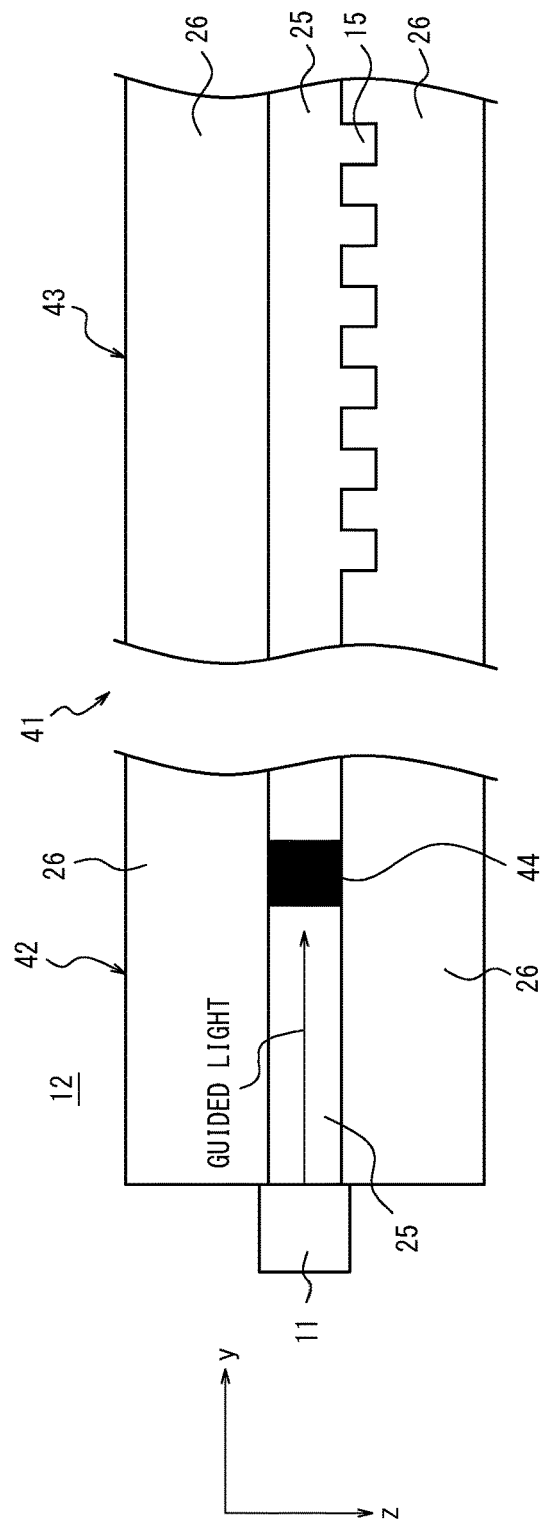
FIG. 17B is an enlarged schematic diagram of an optical waveguide optical system viewed from the x-direction, the system having the slab optical waveguide in Configuration Example 4 of the illumination portion.

FIGS. 17A and 17B each are an explanatory diagram of Configuration Example 4 of the illumination portion 10. Configuration Example 4 is different from Configuration Example 3 in that the tapered optical waveguide 42 forming the slab optical waveguide 41 has a conversion grating part 44 for converting the wave front of illumination light propagating therethrough.

FIGS. 17A and 17B are enlarged schematic diagrams of the optical waveguide optical system 12 each viewed from the z-direction and the x-direction, respectively. The conversion grating part 44 is formed at an arbitrary position on the propagation path of illumination light in the tapered optical waveguide 42, and converts, in the x-y plane, illumination light propagating through the tapered optical waveguide 42 from spherical wave to plane wave. The grating part 15 on the rectangular optical waveguide 43 is formed in a predetermined shape (rectangle in the drawing) and with a predetermined period; in the x-y plane, and linearly formed in the x-y plane in line with the plane wave of the illumination light.

When applied to the illumination portion 10 of Example 8 or Example 9, the tapered optical waveguides forming the optical waveguides 33a, 33b, 33c are each configured by having the aforementioned conversion grating part.

The illumination portion 10 of Configuration Example 4 is capable of linearly forming, in the x-y plane, the grating part 15 of the rectangular optical waveguide 43 in line with the plane wave of the illumination light, which provides another advantage, in addition the effect of Configuration Example 3, in that the grating part 15 can be formed with ease. The same applies when Configuration Example 4 is applied to the illumination portion 10 of Embodiment 8 and Embodiment 9.

Configuration Example 5 of Illumination Portion

Figure 18A:
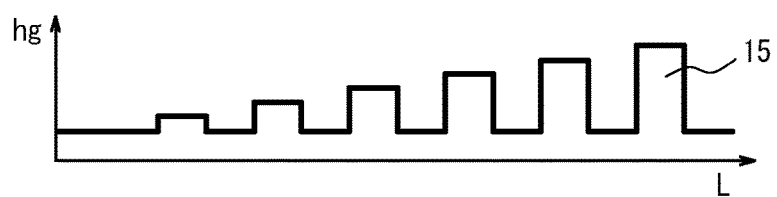
FIG. 18A explains Configuration Example 5 of the illumination portion.

FIG. 18A explains Configuration Example 5 of the illumination portion 10. In Configuration Example 5 is different from Configuration Examples 1 to 4 in that the height hg of the grating part 15 is increased along with the increase of the grating length L in the propagation direction (y-direction) of illumination light.

Figure 18B:
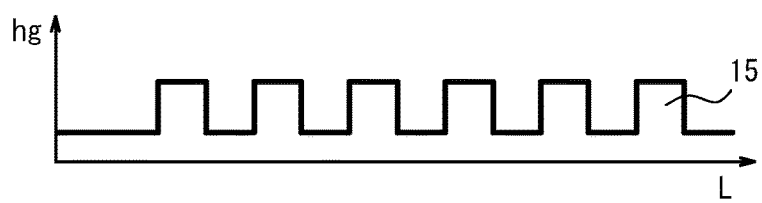
FIG. 18B illustrates a grating with a fixed height.
Figure 19:
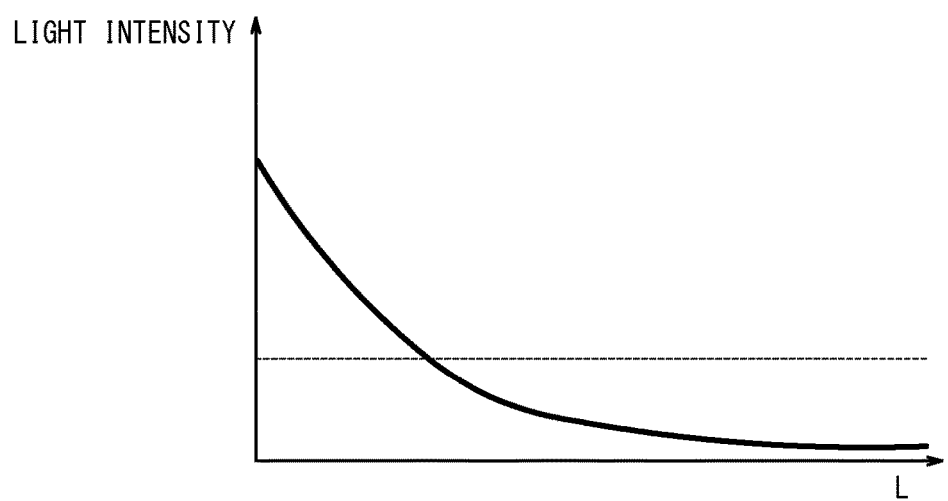
FIG. 19 is a graph illustrating an intensity distribution of illumination light diffracted by the gratings of FIGS. 18A and 18B.

Specifically, as illustrated in FIG. 18B, when the height hg of the grating part 15 is fixed over the grating length L, illumination light diffracted by the grating part 15 and emitted from the illumination portion 10 has an intensity that exponentially attenuates along with the increase of the grating length L in the propagation direction of illumination light, as illustrated by the solid line of FIG. 19. Thus, in Configuration Example 5, the height hg of the grating part 15 is increased along with the increase of the grating length L as illustrated in FIG. 18A, so that illumination light diffracted over the grating length has substantially constant intensity as indicated by the broken line of FIG. 19. The rest of the configuration is similar to those of Configuration Examples above.

Accordingly, when applied to Configuration Example 1, illumination light in a plane waveform can be emitted in a longer band shape at a substantially constant intensity. When applied to Configuration Examples 2 to 4, illumination light in a plane waveform can be emitted at a substantially constant intensity in a plane with a large area elongated in the propagation direction, over a wider field of view.

When applied to the illumination portion 10 of Embodiment 8 or Embodiment 9, the optical waveguide optical systems 32a, 32b, 32c are layered from the light emission surface 34D side opposing to the object holder 60 in the ascending order of the wavelength to be emitted, as described above. Accordingly, the grating parts 35a, 35b, 35c may be increased in height hg along with the increase of the grating length L, which can still prevent the generation of diffracted light in unnecessary orders, which may otherwise be generated when illumination light emitted from an optical waveguide optical system in the upper layer passes through an optical waveguide optical system in the lower layer.

The disclosed apparatus is not limited to Embodiments above, and may be subjected to various modifications and alterations without departing from the gist of the disclosure. For example, Embodiments 6 and 7 may be configured to emit, not only the illumination lights of three colors of R, G, and B, illumination light of arbitrary two or four or more colors in different directions. Further, in Embodiment 8, two or at least 4 layers of the optical waveguide optical system may be provided, so as to emit illumination light of the same wavelength in different directions. Similarly, in Embodiment 9, without being limited to the illumination light of three colors of R, G, B, two or at least four layers of the optical waveguide optical systems may be provided to emit illumination light of arbitrary two colors or four or more colors in different directions.

REFERENCE SIGNS LIST 1 object
10 illumination portion
11 light source
12 optical waveguide optical system
13 optical waveguide
14U, 14D light emission surface
15 grating part
20, 30 light source portion
31a, 31b, 31c light source
32a, 32b, 32c optical waveguide optical system
33a, 33b, 33c optical waveguide
34U, 34D light emission surface
35a, 35b, 35c grating part
50 image sensor
51 pixel array
52 cover glass
53 color filter
60 object holder
61 object contact surface
70 container
80 arithmetic portion

The invention claimed is:

1. A digital holographic image-taking apparatus, comprising:
an illumination portion comprising a light source that emits illumination light of a specific wavelength and a light emission surface from which the illumination light is emitted toward an object as a coherent plane waveform;
an object holder capable of holding the object; and
an image sensor having a pixel array including two-dimensionally arranged pixels, the image sensor capturing an interference pattern generated based on the illumination light having acted on the object,
wherein the illumination portion, the object holder, and the image sensor are positioned with respect to each other such that the following conditional expressions are satisfied:

$$0.0000001 < Z^2/S < 16$$

$$0.0000001 \leq Z_{10}^2/S < 4$$

$$0.0000001 < Z_{20}^2/S < 4$$

where:
S represents an area of the light emission surface;
Z represents a distance from the light emission surface to the pixel array;
$Z_{10}$ represents a distance from the light emission surface to an object contact surface of the object holder; and
$Z_{20}$ represents a distance from the object contact surface to the pixel array.

2. The digital holographic image-taking apparatus according to claim 1, wherein the illumination portion, the object holder, and the image sensor are positioned with respect to each other such that the following conditional expression is satisfied:

$$0.25 < Z_{10}/Z_{20} < 4.$$

3. The digital holographic image-taking apparatus according to claim 1, wherein the pixels of the image sensor are each arranged along a plane substantially parallel to the light emission surface.

4. The digital holographic image-taking apparatus according to claim 1, further comprising an arithmetic portion that analyzes the object based on an output of the image sensor.

5. The digital holographic image-taking apparatus according to claim 1, wherein the illumination portion further comprises an optical waveguide optical system, the optical waveguide optical system comprising:
an optical waveguide that propagates the illumination light from the light source by causing the illumination light to be repeatedly reflected alternately between two opposing planes; and
a grating part that diffracts the illumination lights propagating through the optical waveguide so as to cause the illumination lights to be emitted in a same direction from the light emission surface.

6. The digital holographic image-taking apparatus according to claim 1, wherein the illumination portion emits, toward a plurality of directions from the light emission surface, illumination lights each in a coherent plane waveform.

7. The digital holographic image-taking apparatus according to claim 6, wherein the illumination portion emits a plurality of illumination lights of different peak wavelengths.

8. The digital holographic image-taking apparatus according to claim 7, wherein the light source sequentially emits the plurality of illumination lights, and
wherein the illumination portion further comprises an optical waveguide optical system, the optical waveguide optical system comprising:
an optical waveguide that propagates the illumination lights from the light source by causing the illumination lights to be repeatedly reflected alternately between two opposing planes; and
a grating part portion that diffracts the illumination lights propagating through the optical waveguide so as to cause the illumination lights to be emitted from the light emission surface in different directions for the respective peak wavelengths.

9. The digital holographic image-taking apparatus according to claim 7, wherein the light source emits the plurality of illumination lights simultaneously,
wherein the illumination portion further comprises an optical waveguide optical system, the optical waveguide optical system comprising:
an optical waveguide that propagates the illumination lights emitted from the light source by causing the illumination lights to be repeatedly reflected alternately between two opposing planes; and
a grating part that diffracts the illumination lights propagating through the optical waveguide so as to cause the illumination lights to be emitted from the light emission surface in different directions for the respective peak wavelengths, and
wherein the image sensor comprises a color filter having a spectral sensitivity characteristic corresponding to the peak wavelengths of the plurality of illumination lights.

10. The digital holographic image-taking apparatus according to claim 7, wherein the light source that emits the plurality of lights simultaneously,
wherein the illumination portion further comprises a plurality of layered optical waveguide optical systems which correspond to the plurality of illumination lights, each of the plurality of optical waveguide optical systems comprising:
an optical waveguide that propagates the illumination lights emitted from the light source by causing the illumination lights to be repeatedly reflected alternately between two opposing planes; and
a grating part that diffracts the illumination lights propagating through the optical waveguide so as to cause the illumination lights to be emitted in a same direction from the light emission surface, and
wherein the image sensor comprises a color filter having a spectral sensitivity characteristic corresponding to the peak wavelengths of the plurality of illumination lights.

11. The digital holographic image-taking apparatus according to claim 10, wherein the plurality of optical waveguide optical systems are layered from the light emission surface side, in ascending order of the peak wavelengths of the corresponding illumination lights.

12. The digital holographic image-taking apparatus according to claim 6, wherein the illumination portion emits illumination lights of equal peak wavelength.

13. The digital holographic image-taking apparatus according to claim 12, wherein the illumination portion further comprises a plurality of optical waveguide optical systems layered as corresponding to the emission directions of the illumination lights from the light emission surface, the light source causing the illumination lights to be sequentially incident on the plurality of optical waveguide optical systems, and each of the plurality of optical waveguide optical systems comprising:

an optical waveguide propagating the illumination lights emitted from the light source by causing the illumination lights to be repeatedly reflected alternately between two opposing planes; and
a grating part that diffracts the illumination light propagating through the optical waveguide so as to cause the illumination lights to be emitted from the light emission surface in different directions.

14. The digital holographic image-taking apparatus according to claim 1, wherein the image sensor is disposed at a position where the interference pattern is incident, the interference pattern being formed by the illumination light which has been emitted from the light emission surface and passed through the object.

15. The digital holographic image-taking apparatus according to claim 14, wherein the image sensor is disposed at a position where the illumination light that has passed through the object is directly incident.

16. The digital holographic image-taking apparatus according to claim 1, wherein:
the illumination portion further comprises an opposing light emission surface provided opposite to the light emission surface, the opposing light emission surface emitting illumination light in a direction opposite to a direction in which the light emission surface emits the illumination light; and
the image sensor is disposed at a position where the interference pattern is incident, the interference pattern being formed between (i) the illumination light emitted from the opposing light emission surface, and (ii) the illumination light emitted from the light emission surface and reflected by the object so as to pass through the light emission surface and the opposing light emission surface.

17. The digital holographic image-taking apparatus according to claim 16, wherein the image sensor is coupled to the opposing light emission surface.

18. The digital holographic image-taking apparatus according to claim 1, wherein the illumination portion, the object holder, and the image sensor are positioned with respect to each other such that the following conditional expressions are satisfied:

$0.001 < Z^2/S < 1$ $0.001 \leq Z_{10}^2/S < 1$ $0.001 < Z_{20}^2/S < 1.$

19. The digital holographic image-taking apparatus according to claim 1, wherein the illumination portion, the object holder, and the image sensor are positioned with respect to each other such that the following conditional expressions are satisfied:

$0.001 < Z^2/S < 1$ $0.001 \leq Z_{10}^2/S < 0.5$ $0.001 < Z_{20}^2/S < 0.5.$

* * * * *